United States Patent [19]

Kormany

[11] 4,167,628

[45] Sep. 11, 1979

[54] NOVEL BENZOXAZOLE COMPOUNDS

[75] Inventor: Geza Kormany, Allschwil, Switzerland

[73] Assignee: Ciba-Geigy Corporation, Ardsley, N.J.

[21] Appl. No.: 858,989

[22] Filed: Dec. 9, 1977

[30] Foreign Application Priority Data

Dec. 23, 1976 [LU] Luxembourg .......................... 76467

[51] Int. Cl.$^2$ .................. C07D 413/02; C07D 263/54
[52] U.S. Cl. ............................. 542/454; 252/301.24; 542/429; 542/430; 542/455; 542/456; 542/459; 542/464; 542/466; 427/158; 548/113; 548/224
[58] Field of Search ............... 542/459, 464, 429, 430, 542/455, 456, 454, 466; 260/307 D; 252/301.24; 427/158

[56] References Cited

U.S. PATENT DOCUMENTS

| | | | |
|---|---|---|---|
| 2,985,661 | 5/1961 | Hein | 260/307 D |
| 3,076,812 | 2/1963 | Ackermann et al. | 260/307 D |
| 3,274,184 | 9/1966 | Thompson | 542/455 |
| 3,413,233 | 11/1968 | Siegrist et al. | 252/301.2 |
| 3,711,472 | 1/1973 | Siegrist et al. | 260/240 C X |
| 3,725,395 | 4/1973 | Siegrist et al. | 542/459 |
| 3,732,221 | 5/1973 | Siegrist et al. | 260/240 B |
| 3,781,278 | 12/1973 | Siegrist et al. | 260/240 C X |

FOREIGN PATENT DOCUMENTS

| | | | |
|---|---|---|---|
| 850008 | 7/1952 | Fed. Rep. of Germany | 260/307 D |
| 1445916 | 4/1969 | Fed. Rep. of Germany | 260/307 D |
| 508009 | 7/1971 | Switzerland | |
| 902058 | 7/1962 | United Kingdom | |
| 902059 | 7/1962 | United Kingdom | |

OTHER PUBLICATIONS

Liechtl et al., Chem. Abstr., 75 (1971), #141978.
Siegrist et al., Chem. Abstr. 72 (1970), #91492.

*Primary Examiner*—Arthur P. Demers
*Attorney, Agent, or Firm*—Prabodh I. Almaula

[57] ABSTRACT

Novel benzoxazole compounds of the formula

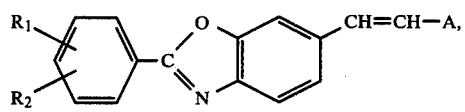

wherein $R_1$, $R_2$ and A are certain substituents, a process for their manufacture as well as their use as optical brighteners are disclosed.

19 Claims, No Drawings

NOVEL BENZOXAZOLE COMPOUNDS

The present invention provides novel 2-phenyl-6-styrylbenzoxazole- and 1-(2-phenyl-benzoxazolyl)-2-benzoxazolylethylene compounds, processes for their manufacture, and a method of optically brightening high molecular organic materials which comprises the use of said compounds.

The compounds of the present invention have the formula

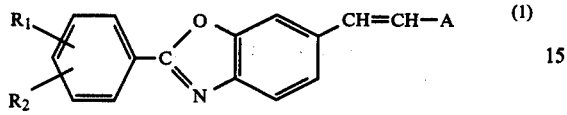

wherein $R_1$ represents hydrogen, halogen, cyano, alkyl of 1 to 8 carbon atoms, cyclohexyl, alkyl of 1 to 4 carbon atoms which is substituted by halogen, cyano, alkoxy of 1 to 4 carbon atoms or phenyl, while the phenyl moiety of a phenylalkyl radical can contain in addition one or two substituents selected from the group consisting of halogen, methyl or methoxy; alkoxy of 1 to 4 carbon atoms which is unsubstituted or substituted by cyano or alkoxy of 1 to 4 carbon atoms; phenyl or phenoxy which is unsubstituted or substituted by one or two radicals selected from the group consisting of halogen, cyano, alkyl or alkoxy, each of 1 to 4 carbon atoms; the sulpho group and the derivatives thereof; the carboxyl group and the derivatives thereof; a sulphonyl group; or together with $R_2$ in the ortho-position represents an alkylene radical of 3 or 4 carbon atoms or the butadienylene radical, $R_2$ represents hydrogen, alkyl of 1 to 6 carbon atoms, alkoxy of 1 to 4 carbon atoms, halogen, or together with $R_1$ in the ortho-position represents an alkylene radical of 3 or 4 carbon atoms or the butadienylene radical, and A represents a group of the formula

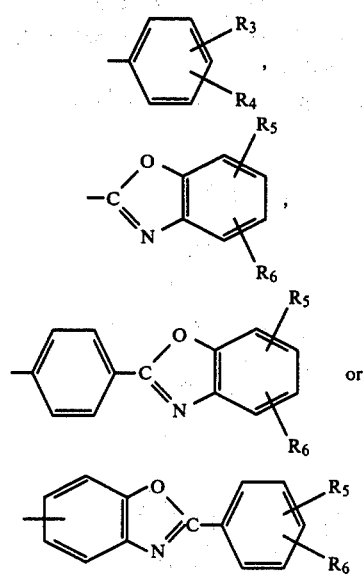

wherein $R_3$ represents a carboxyl group and the derivatives thereof, a sulpho group and the salts thereof, a sulphonyl or cyano group, $R_4$ represents hydrogen, alkyl of 1 to 6 carbon atoms, alkoxy of 1 to 4 carbon atoms, halogen, the sulpho group and the salts thereof or the carboxyl group and the derivatives thereof, $R_5$ represents hydrogen, alkyl of 1 to 8 carbon atoms, alkyl of 1 to 4 carbon atoms which is substituted by halogen, cyano, alkoxy of 1 to 4 carbon atoms or phenyl, while the phenyl moiety of a phenylalkyl radical can contain in addition one or two substituents selected from the group consisting of halogen, methyl or methoxy; cyclohexyl, alkoxy of 1 to 4 carbon atoms which is unsubstituted or substituted by cyano or alkoxy of 1 to 4 carbon atoms; phenyl or phenoxy which is unsubstituted or substituted by one or two radicals selected from the group consisting of halogen, cyano, alkyl or alkoxy, each of 1 to 4 carbon atoms; halogen, cyano, sulphonyl, the carboxyl group or the derivatives thereof, the sulpho group or the derivatives thereof; or together with $R_6$ in the ortho-position represents an alkylene radical of 3 or 4 carbon atoms or the butadienylene radical; and $R_6$ represents hydrogen, alkyl of 1 to 6 carbon atoms, alkoxy of 1 to 4 carbon atoms, halogen, or together with $R_5$ in the ortho-position represents an alkylene radical of 3 or 4 carbon atoms or the butadienylene radical.

The term "halogen" is to be understood as meaning all halogen atoms, but preferably chlorine or bromine, in particular chlorine.

Preferred derivatives of the carboxyl and sulpho groups are salts, esters and amides.

Throughout this specification, a salt-forming cation is to be understood as meaning an alkali metal, alkaline earth metal, ammonium, or amine salt ion. The alkali metal ions are preferred, in particular the sodium and potassium ion.

Compounds of particular interest within the scope of the formula (1) are those of the formula

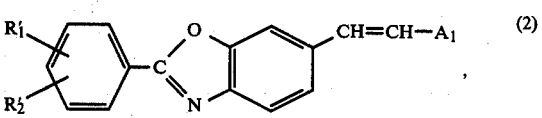

wherein $R_1'$ represents hydrogen, alkyl of 1 to 4 carbon atoms, cyanoalkyl containing 1 to 3 carbon atoms in the alkyl moiety, alkoxyalkyl having a total of 2 to 6 carbon atoms, halogen, cyano, benzyl, alkoxy of 1 to 4 carbon atoms, alkoxyalkoxy having a total of 2 to 6 carbon atoms, phenyl, phenoxy, carbalkoxy of 2 to 5 carbon atoms, the carboxyl group and the alkali metal, alkaline earth metal, ammonium and amine salts thereof, or together with $R_2'$ in the ortho-position represents the butadienylene radical, $R_2'$ represents hydrogen, alkyl of 1 to 4 carbon atoms, halogen, alkoxy of 1 to 4 carbon atoms, or together with $R_1'$ in the ortho-position represents the butadienylene radical; and $A_1$ represents a group of the formula

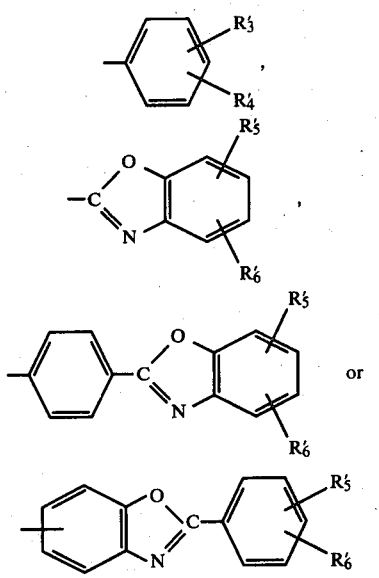

(2a)

(2b)

(2c) or (2d)

wherein
R$_3'$ represents alkylsulphonyl of 1 to 4 carbon atoms, cyano, a group of the formula —COOY, in which Y represents hydrogen, alkyl of 1 to 4 carbon atoms or an alkali metal, alkaline earth metal, ammonium or amine ion; or represents a group of the formula —SO$_3$Y$_1$, in which Y$_1$ represents hydrogen, an alkali metal, alkaline earth metal, ammonium or amine ion, R$_4'$ represents hydrogen, alkyl of 1 to 4 carbon atoms, alkoxy of 1 to 4 carbon atoms, halogen, or the sulpho group and the alkali metal salts thereof, R$_5'$ represents hydrogen, alkyl of 1 to 4 carbon atoms, alkoxyalkyl having a total of 2 to 6 carbon atoms, cyanoalkyl containing 1 to 3 carbon atoms in the alkyl moiety, benzyl, alkoxy of 1 to 4 carbon atoms, alkoxyalkoxy of 2 to 6 carbon atoms, phenyl, phenoxy, halogen, cyano, alkylsulphonyl of 1 to 4 carbon atoms, a group of the formula —COOY, in which Y represents hydrogen, alkyl of 1 to 4 carbon atoms or an alkali metal, alkaline earth metal, ammonium or amine ion; or represents a group of the formula —SO$_3$Y$_1$, in which Y$_1$ represents hydrogen, an alkali metal, alkaline earth metal, ammonium or amine ion, a group of the formula

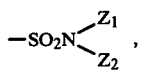

in which Z$_1$ represents hydrogen, alkyl of 1 to 4 carbon atoms, alkoxyalkyl having a total of 2 to 6 carbon atoms, cyanoalkyl containing 1 to 3 carbon atoms in the alkyl moiety, Z$_2$ has the meaning of Z$_1$ and in addition represents benzyl, or Z$_1$ or Z$_2$ together with the nitrogen atom to which they are attached form a morpholine or piperidine ring, or together with R$_6'$ in the ortho-position represent the butadienylene radical; and R$_6'$ represents hydrogen, alkyl of 1 to 4 carbon atoms, alkoxy of 1 to 4 carbon atoms or halogen, or together with R$_5'$ in the ortho-position represents the butadienylene radical, and especially those of the formula

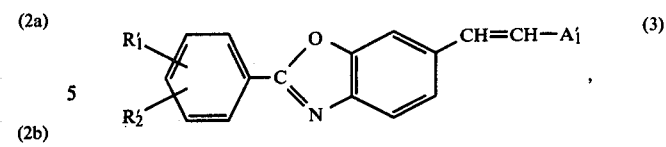

(3)

wherein R$_1'$ and R$_2'$ are as defined in formula (2) and A$_1'$ represents a group of the formula

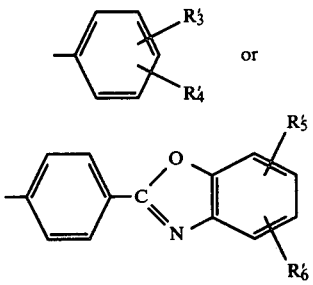

(3a) or (3b)

wherein R$_3'$, R$_4'$, R$_5'$ and R$_6'$ are as defined in formula (2).

Compounds to be highlighted are also the benzoxazoles of the formula

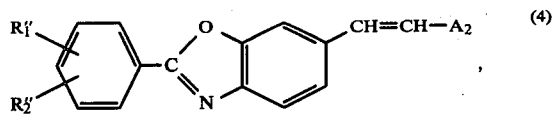

(4)

wherein
R$_1''$ represents hydrogen, alkyl of 1 to 4 carbon atoms, halogen, cyano, alkoxy of 1 to 4 carbon atoms, phenyl, the carboxyl group and the alkali metal salts thereof, carbalkoxy of 2 to 5 carbon atoms, or together with R$_2''$ in the ortho-position represents the butadienylene radical, R$_2''$ represents hydrogen, alkyl of 1 to 4 carbon atoms, halogen, alkoxy of 1 to 4 carbon atoms, or together with R$_1''$ in the ortho-position represents the butadienylene radical, and A$_2$ represents a group of the formula

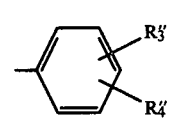

(4a)

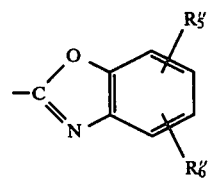

(4b)

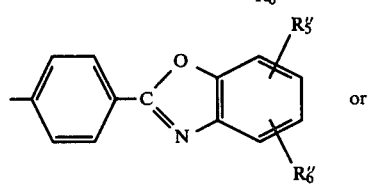

(4c) or

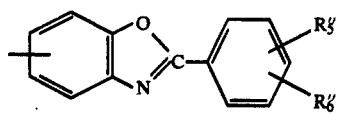

wherein
- $R_3''$ represents alkylsulphonyl of 1 to 4 carbon atoms, cyano, the carboxyl group and the alkali metal salts thereof, carbalkoxy of 2 to 5 carbon atoms, the sulpho group and the alkali metal salts thereof,
- $R_4''$ represents hydrogen, alkyl of 1 to 4 carbon atoms, alkoxy of 1 to 4 carbon atoms, halogen, or the sulpho group and the alkali metal salts thereof,
- $R_5''$ represents hydrogen, alkyl of 1 to 4 carbon atoms, alkoxyalkyl having a total of 2 to 6 carbon atoms, cyanoalkyl containing 1 to 3 carbon atoms in the alkyl moiety, alkoxy of 1 to 4 carbon atoms, phenyl, halogen, cyano, alkylsulphonyl of 1 to 4 carbon atoms, the carboxyl group and the alkali metal salts thereof, carbalkoxy of 2 to 5 carbon atoms, the sulpho group and the alkali metal salts thereof; and
- $R_6''$ represents hydrogen, alkyl of 1 to 4 carbon atoms, alkoxy of 1 to 4 carbon atoms or halogen, especially those of the formula

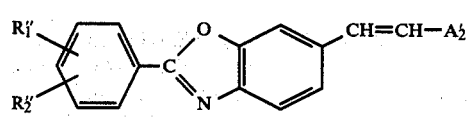

wherein $R_1''$ and $R_2''$ are as defined in formula (4) and $A_2'$ represents a group of the formula

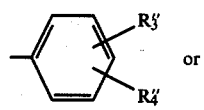

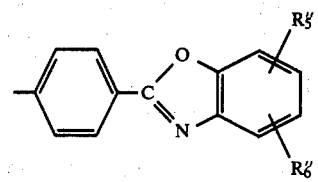

wherein $R_3''$, $R_4''$, $R_5''$ and $R_6''$ are as defined in formula (4).

Compounds having a particularly interesting utility are those of the formula

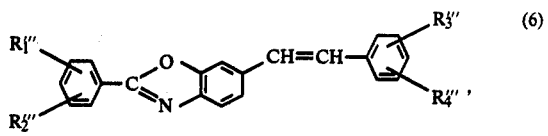

wherein
- $R_1'''$ represents hydrogen, alkyl of 1 to 4 carbon atoms, halogen, cyano, alkoxy of 1 to 4 carbon atoms, or phenyl,
- $R_2'''$ represents hydrogen, alkyl of 1 to 4 carbon atoms, halogen, or alkoxy of 1 to 4 carbon atoms,
- $R_3'''$ represents alkylsulphonyl of 1 to 4 carbon atoms, cyano, the carboxyl group and the alkali metal salts thereof, carbalkoxy of 2 to 5 carbon atoms, or the sulpho group and the alkali metal salts thereof; and
- $R_4'''$ represents hydrogen, alkyl of 1 to 4 carbon atoms, alkoxy of 1 to 4 carbon atoms, halogen, or the sulpho group and the alkali metal salts thereof, in particular those of the formula

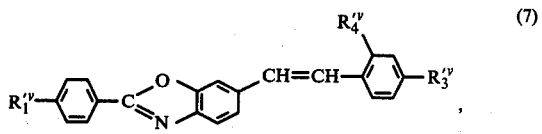

wherein
- $R_1^{iv}$ represents hydrogen, chlorine, phenyl, or alkoxy of 1 to 4 carbon atoms,
- $R_3^{iv}$ represents alkylsulphonyl of 1 to 4 carbon atoms, carbalkoxy of 2 to 5 carbon atoms, cyano, or the sulpho group and the alkali metal salts thereof, and
- $R_4^{iv}$ represents hydrogen or the sulpho group and the alkali metal salts thereof, and also compounds of the formula

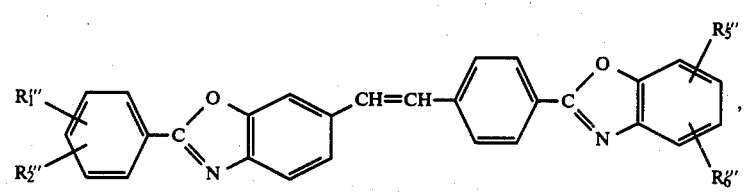

wherein
- $R_1'''$ represents hydrogen, alkyl of 1 to 4 carbon atoms, halogen, cyano, alkoxy of 1 to 4 carbon atoms or phenyl,
- $R_2'''$ represents hydrogen, alkyl of 1 to 4 carbon atoms, halogen or alkoxy of 1 to 4 carbon atoms,
- $R_5'''$ represents hydrogen, alkyl of 1 to 4 carbon atoms, cyanoalkyl containing 1 to 3 carbon atoms in the alkyl moiety, alkoxy of 1 to 4 carbon atoms, phenyl, chlorine or cyano; and
- $R_6'''$ represents hydrogen, alkyl of 1 to 4 carbon atoms, alkoxy of 1 to 4 carbon atoms or chlorine, in particular those of the formula

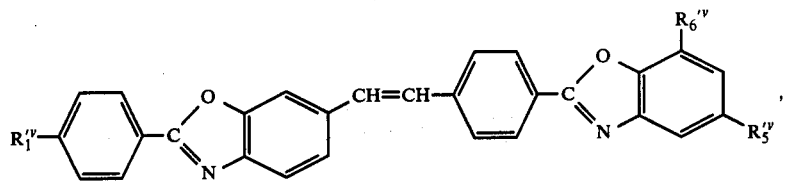
(9)

wherein
- $R_1^{iv}$ represents hydrogen, chlorine, alkoxy of 1 to 4 carbon atoms, or phenyl,
- $R_5^{iv}$ represents hydrogen, chlorine or alkyl of 1 to 4 carbon atoms, and
- $R_6^{iv}$ represents hydrogen or alkyl of 1 to 4 carbon atoms.

To be mentioned are also compounds of the formula

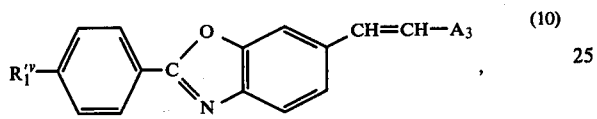
(10)

wherein
- $R_1^{iv}$ represents hydrogen, chlorine, alkoxy of 1 to 4 carbon atoms or phenyl, and
- $A_3$ represents a group of the formula

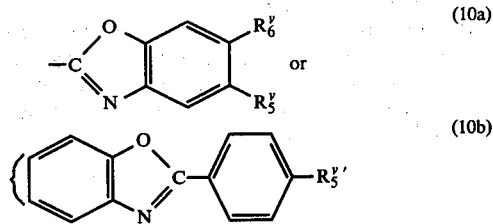
(10a)

or (10b)

wherein
- $R_5^v$ represents hydrogen, alkyl of 1 to 4 carbon atoms, cyanoalkyl having a total of 2 or 3 carbon atoms, or phenyl,
- $R_6^v$ represents hydrogen or alkyl of 1 to 4 carbon atoms, and
- $R^{vi}$ represents hydrogen, chlorine, or alkoxy of 1 to 4 carbon atoms.

The novel benzoxazole compounds of the formulae (1) to (10) can be prepared by different processes.

The novel compounds of the formula (1), in which A represents a group of the formula (1a), (1c) or (1d), and accordingly also the corresponding compounds of the subformulae, can be obtained by a process which comprises reacting a methyl compound of the formula

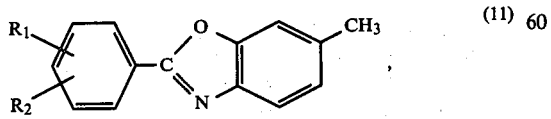
(11)

wherein $R_1$ and $R_2$ are as defined in formula (1), in dimethyl formamide as reaction medium and in the presence of a strong basic alkali compound, with a Schiff's base of the formula

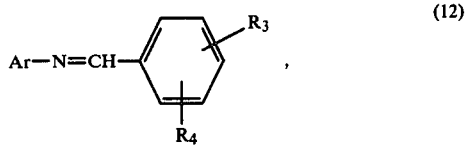
(12)

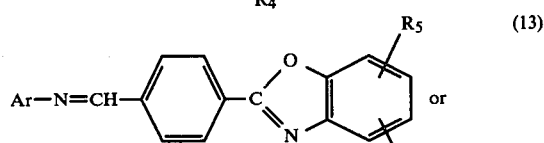
(13)

or

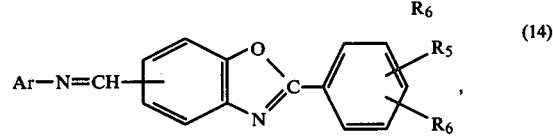
(14)

wherein $R_3$, $R_4$, $R_5$ and $R_6$ are as defined in formula (1) and Ar represents an aromatic radical. The reaction mixture can initially be irradiated with UV light.

The irradiation with UV light is effected by means of a light source which is additionally applied either externally or within the reaction vessel. The irradiation with UV light can be used to initiate the reaction and not to bring the reaction of the reactants to full completion. An irradiation of a few minutes therefore usually suffices. Preferably, ultraviolet light having a wavelength of more than 300 μm is used.

The symbol Ar represents in general a substituted or unsubstituted phenyl radical. Preferably, Ar represents the radical of the formula

(15)

wherein h represents hydrogen or chlorine.

A strong basic alkali compound is in general one of the formula

(16) $MO_{n-1}H_{2n-1}$, wherein M is potassium or sodium and n is an integer from 1 to 6, and is for example sodium methylate, potassium tert-butylate, sodium hydroxide and potassium hydroxide.

If an alcoholate is used, the process is carried out in virtually anhydrous medium, whereas if a hydroxide is used, a water content of up to 25% is permissable. On using potassium hydroxide, the use of which is preferred, a water content of up to about 15% is advantageous.

It is advantageous to react the methyl compound with the Schiff's base in equivalent amounts, so that there is no substantial excess of any component. Preferably, at least the equivalent amount of alkali compound is used, i.e. 1 mole of alkali compound per 1 mole of Schiff's base. In the case of potassium hydroxide, preferably a two- to eight-fold equivalent amount is used.

The reaction of the present invention can usually be carried out in a temperature range between about 0° and 100° C., preferably between 10° and 60° C. The end products can be isolated from the reaction mixture by conventional methods which are known per se.

The starting materials of the formulae (11), (12), (13) and (14) are obtained by methods analogous to known ones (vide the Examples).

The compounds of the formula (1), wherein A represents the group of the formula (1b), and thus also the compounds of the corresponding subformulae, can be prepared by reacting a compound of the formula

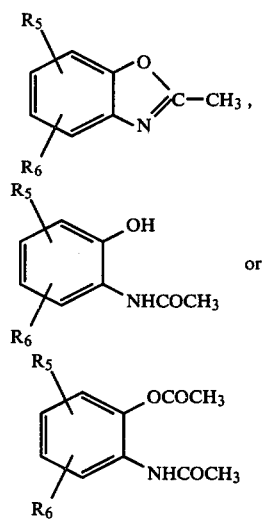

wherein $R_5$ and $R_6$ have the above meanings, with an aldehyde of the formula

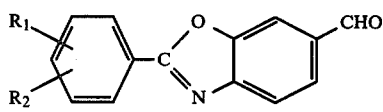

wherein $R_1$ and $R_2$ have the above meanings, in the presence of a catalyst which splits off water and in an inert high-boiling solvent, while simultaneously removing the water of reaction.

To prepare the compounds last mentioned, it is also possible to start from the corresponding o-aminophenols and to obtain the above compounds by means of a process which is carried out in a single operation in the same reaction vessel. This mode of reaction is new and is not described in the literature.

The procedure comprises reacting an o-aminophenol of the formula

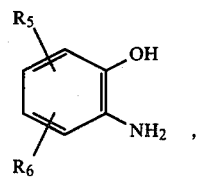

wherein $R_5$ and $R_6$ have the given meanings, in an inert high-boiling solvent, with acetic anhydride and an aldehyde of the formula (20) in the presence of a catalyst which splits off water. The reaction is carried out without isolation of the intermediate. The water of reaction is preferably removed from the reaction mixture using a water separator.

Suitable catalysts which split off water for both the above described processes are for example zinc chloride, acetic anhydride, or an arylsulphonic acid, for example toluene-4-sulphonic acid, with or without the addition of a dialkylamide, such as dimethyl formamide or dimethyl acetamide.

As inert high-boiling solvent it is possible to use for example a high-boiling, preferably aromatic, hydrocarbon or a halogenated hydrocarbon, such as xylene, chlorobenzene or dichlorobenzene.

Both the above reactions with the aldehyde of the formula (20) are preferably carried out at elevated temperature, for example at the boiling temperature of the solvent employed.

The starting materials of the formulae (17) to (21) are known or they can be prepared by methods which are known per se (vide the Examples). Another method, which is known per se, of obtaining the novel compounds of the formula (1) in which A represents a group of the formula (1a), (1c) or (1d), and thus also of the corresponding subformulae, consists in reacting a compound of the formula

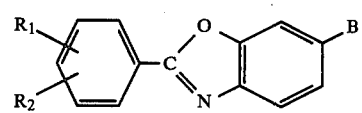

with a compound of the formula

(23) B₁—A' wherein $R_1$ and $R_2$ have the given meanings, and A' represents a group of the formula

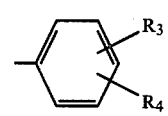

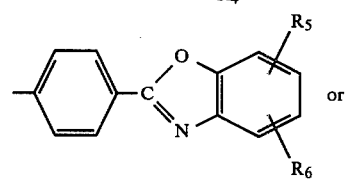

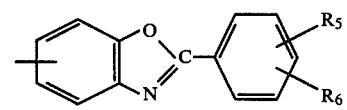

wherein $R_5$ and $R_6$ are as defined in formula (1), and one of the two symbols B and $B_1$ represents a

group and the other represents a group of the formula

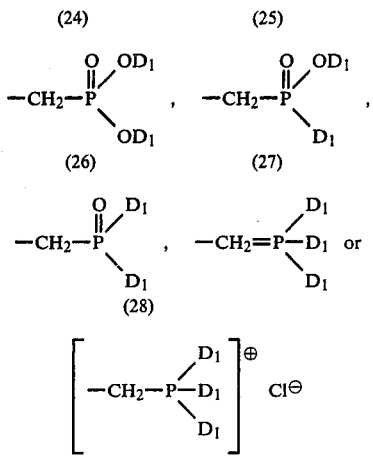

wherein $D_1$ represents an alkyl radical which can be further substituted, preferably one containing not more than 4 carbon atoms, an aryl radical, preferably a phenyl radical, a cycloalkyl radical, preferably a cyclohexyl radical, or an aralkyl radical, preferably a benzyl radical.

This process is advantageously carried out in an inert solvent, for example a hydrocarbon, such as toluene and xylene, or an alcohol, such as methanol, ethanol, isopropanol, butanol, butanol, a glycol, a glycol ether, such as 2-methoxyethanol, a hexanol, cyclohexanol and cyclooctanol, and an ether, such as diisopropyl ether, tetrahydrofurane and dioxane, as well as dimethyl sulphoxide, formamide and N-methylpyrrolidone. Particularly suitable solvents are polar organic solvents, such as dimethyl formamide and dimethyl sulphoxide. Some of the reactions can also be carried out in aqueous solution.

The temperature at which the reaction is carried out can vary within wide limits. It is determined by
 (α) the resistance to the reactants of the solvents employed, especially to the strong basic alkali compounds,
 (β) the reactivity of the condensation partners, and
 (γ) the strength of the combination of solvent and base as condensation agent.

In practice, temperatures between 0° and 100° C. are therefore suitable as a rule, especially if ether dimethyl formamide or dimethyl sulphoxide is used as solvent. The preferred temperature range is between 10° and 60° C.

The reaction is preferably carried out in the presence of strong basic alkali compounds. Suitable strong basic alkali compounds are in particular the hydroxides, amides and alcoholates of alkali metals, those of lithium, sodium and potassium being of primary interest. However, in principle and in special cases, it is also possible to use with success alkali sulphides and carbonates, arylalkali compounds, for example phenyl lithium, or strong basic amines, for example trialkylammonium hydroxides.

The starting materials of the formulae (22) to (28) are known or they can be prepared by methods analogous to known ones (vide the Examples).

The novel compounds defined above exhibit a more or less pronounced fluorescence in solution or dispersion. They can be used for optically brightening a wide variety of synthetic, regenerated man-made, or natural organic materials, or substances which contain such organic materials.

Without any restriction being implied by the following classification, examples of organic materials which can be optically brightened are:

I. Synthetic organic materials of high molecular weight:

(a) polymerisation products based on organic compounds containing at least one polymerisable carbon-carbon double bond, that is to say their homopolymers or copolymers as well as their aftertreatment products, for example, crosslinking, grafting or degradation products, polymer blends, or products obtained by modification of reactive groups, for example polymers based on α,β-unsaturated carboxylic acids or derivatives of such carboxylic acids, especially on acrylic compounds, for example acrylates, acrylic acid, acrylonitrile, acrylamides and their methacrylic analogues), on olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) polymerisation products which can be obtained by ring opening, for example, polyamides of the polycaprolactam type, and also polymers which are obtained both by polyaddition and by polycondensation, for example polyethers or polyacetals;

(c) polycondensation products or precondensates based on bifunctional or polyfunctional compounds with condensable groups, the homocondensation and co-condensation products, and aftertreatment products thereof, for example polyesters, in particular saturated polyesters (for example polyesters of ethylene glycol terephthalic acid or unsaturated polyesters (for example maleic acid-dialcohol polycondensates and their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, the precondensates and analogues thereof, polycarbonates and silicones;

(d) polyaddition products, such as polyurethanes (crosslinked and uncrosslinked) and epoxide resins.

II. Regenerated man-made organic materials, for example, cellulose esters of varying degrees of esterification (so-called 2½-acetate or triacetate) or cellulose ethers, regenerated cellulose (viscose or cuprammonium cellulose), or their aftertreatment products, and casein plastics.

III. Natural organic materials of animal or vegetable origin, for example based on cellulose or proteins, such as cotton, wool, linen, silk, varnish gums, starch and casein.

The organic materials to be optically brightened can be in the most diverse states of processing (raw materials, semi-finished goods or finished goods). On the other hand, they can be in the form of structures of the most diverse shapes, for example predominantly three-dimensionally expanded structures, such as sheets, profiles, injection mouldings, various machined articles, chips, granules or foams, and also predominently two-dimensional structures, such as films, foils, lacquers, coatings and impregnations or predominantly one-dimensional bodies, such as filaments, fibres, flocks and wires. The said materials can, on the other hand, also be in an unshaped state, in the most diverse homogeneous or inhomogeneous forms of division, as for example in the form of powders, solutions, emulsions, dispersions, latices, pastes or waxes.

Fibrous materials can be, for example, in the form of endless filaments (stretched or unstretched), staple fibres, flocks, hanks, textile filament yarns, threads, non-wovens, felts, waddings, flocked structures or woven textile or bonded textile fabrics, knitted fabrics and papers, cardboards or paper pulps.

The compounds to be used according to the invention are of importance, inter alia, for the treatment of organic textile materials, especially woven textile fabrics. If fibres which can be in the form of staple fibres or endless filaments or in the form of hanks, woven fabrics, knitted fabrics, fleeces, flocked substrates or bonded fabrics, are to be optically brightened according to the invention, this is advantageously effected in an aqueous medium, wherein the compounds in question are present in a finely divided form (suspensions, so-called microdispersions, or optionally solutions). If desired, dispersing agents, stabilisers, wetting agents and further assistants can be added during the treatment.

Depending on the type of brightener compound used, it can be advantageous to carry out the treatment in a neutral or alkaline or acid bath. The treatment is usually carried out at temperatures between 20° and 140° C., for example at the boiling point of the bath or near it (about 90° C.). Solutions or emulsions in organic solvents can also be used for the finishing according to the invention of textile substrates, as is practised in the dyeing industry in so-called solvent dyeing (pad-thermofixation, or exhaust dyeing processes in dyeing machines).

The fluorescent brightening agents of the present invention can further be added to, or incorporated in, the materials before or during their shaping. Thus they can for example be added to the compression moulding composition or injection moulding composition during the manufacture of films, sheets (for example incorporated in polyvinyl chloride in a roll mill at elevated temperature) or mouldings.

If the fashioning of man-made synthetic or regenerated man-made organic materials is effected by spinning processes or from spinning solutions/melts, the fluorescent brightening agents can be applied by the following processes:

addition to the starting substances (for example monomers) or intermediates (for example precondensates or prepolymers), that is to say before or during the polymerisation, polycondensation or polyaddition,
  sprinkling in powder form on polymer chips or granules for spinning solutions/melts,
  bath dyeing of polymer chips or granules for spinning solutions/melts,
  metered addition to spinning melts or spinning solutions, and
  application to the spun tow before stretching.

The fluorescent brightening agents of the present invention can, for example, also be employed in the following use forms:

(a) in mixtures with dyestuffs (shading) or pigments (coloured pigments or especially, for example, white pigments), or as an additive to dye baths, printing pastes, discharge pastes or reserve pastes, or for the aftertreatment of dyeings, prints or discharge prints;

(b) in mixtures with carriers, wetting agents, plasticisers, swelling agents, antioxidants, ultraviolet stabilisers, heat stabilisers and chemical bleaching agents (chlorite bleach or bleaching bath additives);

(c) in admixture with crosslinking agents or finishing agents (for example starch or synthetic finishes), and in combination with a wide variety of textile finishing processes, especially resin finishes (for example crease-proof finishes such as wash-and-wear, permanent-press or non-iron), as well as flameproof finishes, soft-handle finishes, anti-soiling finishes or antistatic finishes, or antimicrobial finishes;

(d) incorporation of the fluorescent brightening agents into polymeric carriers (polymerisation, polycondensation or polyaddition products, in dissolved or dispersed form, for use, for example, in coating agents, impregnating agents or binders (solutions, dispersions and emulsions) for textiles, non-wovens, papers and leather;

(e) as additives to master batches;

(f) as additives to a wide variety of industrial products in order to render these more marketable (for example improving the appearance of soaps, detergents, pigments);

(g) in combination with other fluorescent brightening substances;

(h) in spinning bath preparations, that is to say as additives to spinning baths which are used for improving the slip for the further processing of synthetic fibres, or from a special bath before the streching of the fibre;

(i) as scintillators for various purposes of a photographic nature, for example for electrophotographic reproduction or supersensitising;

(j) depending on the substitution, as laser dyes.

If the brightening process is combined with textile treatment or finishing methods, the combined treatment can in many cases advantageously be carried out with the aid of appropriate stable preparations which contain the fluorescent brightener compounds in such a concentration that the desired white effect is achieved.

In certain cases, the fluorescent brighteners are made fully effective by an aftertreatment. This can be, for example, a chemical treatment (for example acid treatment), a thermal treatment, or a combined chemical/thermal treatment. Thus, for example, the appropriate procedure to follow in brightening a number of fibre substrates, for example polyester fibres, with the fluorescent brightening agents of the present invention, is to impregnate these fibres with the aqueous dispersions (or optionally also solutions) of the brighteners at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at temperatures between 120° and 225° C., for example by heating in a drying chamber, by ironing within the specified temperature range or by treatment with dry, superheated steam. The drying and dry heat treatment can also be carried out in immediate succession or combined in a single operation.

The amount of fluorescent brightening agent to be used according to the invention, based on the weight of the material to be brightened, can vary within wide limits. A marked and lasting effect can be obtained even with very insignificant amounts, in certain cases 0.0001 percent by weight. But it is also possible to use amounts of up to app. 0.8 percent by weight and, on occasion, up to app. 2 percent by weight. For most practical purposes, it is preferable to use amounts between 0.005 and 0.5 percent by weight.

For various reasons it is often advantageous not to use the fluorescent brighteners by themselves, i.e. pure, but in admixture with a wide variety of assistants and extenders, for example anhydrous sodium sulphate, sodium sulphate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The fluorescent brightening agents of this invention are also particularly suitable for use as additives to wash liquors or heavy duty and domestic detergents, to which they can be added in various ways. They are appropriately added to wash liquors in the form of their solutions in water or organic solvents, or, in a finely divided form, as aqueous dispersions. They are advantageously added to domestic or heavy duty detergents in any stage of the manufacturing process of the detergents, for example to the slurry before the washing powder is atomised, or during the preparation of liquid detergent combinations. They can be added either in the form of a solution or dispersion in water or other solvents or, without assistants, as a dry brightening powder. For example, the brightening agents can be mixed, kneaded or ground with the active detergents and, in this form, admixed with the finishing powder. However, they can also be sprayed in a dissolved or pre-dispersed form onto the finished detergent.

Suitable detergents are the known mixtures of active detergents, for example soap in the form of chips and powders, synthetics, soluble salts of sulphonic acid hemiesters of higher fatty alcohols, arylsulphonic acids with higher and/or multiple alkyl substituents, sulphocarboxylic acid esters of medium to higher alcohols, fatty acid acylaminoalkyl- or acylaminoaryl-glycerol sulphonates and phosphoric acid esters of fatty alcohols. Suitable builders which can be used are, for example, alkali metal polyphosphates and polymetaphosphates, alkali metal pyrophosphates, alkali metal salts of carboxymethylcellulose and other soil redeposition inhibitors, and also alkali metal silicates, alkali metal carbonates, alkali metal borates, alkali metal perborates, nitrilotriacetic acid, ethylenediaminetetraacetic acid, and foam stabilisers, such as alkanolamides of higher fatty acids. The detergents can further contain for example: antistatic agents, fat restorative skin protectives, such as lanolin, enzymes, antimicrobial agents, perfumes and colourants.

The fluorescent brightening agents of this invention have the particular advantage that they are also active in the presence of active chlorine donors, for example, hypochlorite, and can be used without significant loss of effect in wash liquors containing non-ionic washing agents, for example alkylphenolpolyglycol ethers.

The compounds according to the invention are added in amounts of 0.005 to 1% or more, based on the weight of the finished detergent in liquid or powder form.

Wash liquors which contain the indicated amounts of the claimed fluorescent brightening agents impart a brilliant appearance in daylight when used to wash textiles made from cellulose fibres, polyamide fibres, resin-finished cellulose fibres, polyester fibres or wool.

The washing treatment is carried out as for example follows:

The textiles are treated for 1 to 30 minutes at 20° to 100° C. in a wash liquor which contains 1 to 10 g/kg of built-up composite detergent and 0.05 to 1%, based on the weight of the detergent, of the claimed brightening agents. The liquor ratio can be 1:3 to 1:50. After they have been washed, the textiles are rinsed and dried in the usual manner. The wash liquor can contain 0.2 g/l of active chlorine (for example as hypochlorite) or 0.1 to 2 g/l of sodium perborate as a bleaching additive.

In the following Examples, parts and percentages are always by weight, unless otherwise stated. Unless indicated to the contrary, melting points and boiling points are uncorrected.

EXAMPLE 1

A solution of 4.46 g (0.02 mole) of 2-phenyl-6-formyl-benzoxazole of the formula

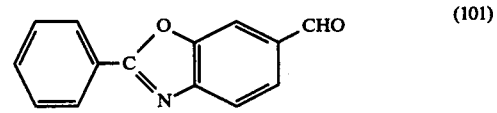

(melting point: 133°–135° C.) and 7.59 g (0.02 mole) of 2-(p-diethylphosphonomethylphenyl)-5-chloro-benzoxazole of the formula

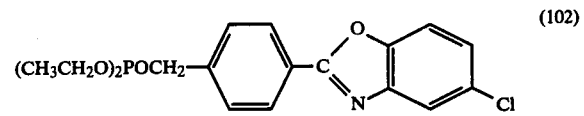

(melting point: 96°–98°) in 80 ml of dimethyl formamide is heated to 40° C. Then 2.1 g (0.022 mole) of sodium tert.butylate are added in small amounts to the solution over the course of 30 minutes and the resultant suspension is further stirred for 4 hours at 40° C. The reaction mixture is poured into water and the precipitate is collected by filtration, washed with water and subsequently with a total amount of 110 ml of methanol. The product is recrystallised form a solvent mixture of nonane/xylene (1:1) with the addition of fuller's earth, affording 3 g (30% of theory) of 1-(2-phenylbenzoxazol-6-yl)-2-[4'-(5-chlorbenzoxazol-2-yl)-phenyl]-ethylene of the formula

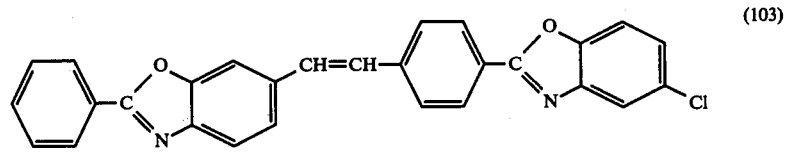

in the form of pale yellow flakes having a melting point of 241°–242° C.

Analysis: $C_{28}H_{17}ClN_2O_2$ (448.9); calculated: C 74.92 H 3.82 N 6.24 Cl 7.90; found: C 74.90 H 4.02 N 6.34 Cl 7.87.

The compounds of the formula

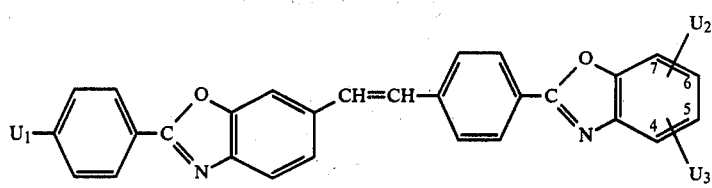

listed in Table 1 are prepared in analogous manner.

Table I

| No. | $U_1$ | $U_2$ | $U_3$ | melting point in °C. |
|---|---|---|---|---|
| 105 | H | H | H | 238 |
| 106 | H | 5-$CH_3$ | 7-$CH_3$ | 217 |
| 107 | H | 5-$C(CH_3)_3$ | H | 222 |
| 108 | Cl | 5-$CH_3$ | 7-$CH_3$ | 240 |
| 109 | Cl | H | H | 263 |
| 110 | $OCH_3$ | H | H | 233 |
| 111 | $OCH_3$ | 5-$CH_3$ | 7-$CH_3$ | 210 |

EXAMPLE 2

A solution of 5.06 g (0.02 Mole) of 2-p-methoxyphenyl-6-formylbenzoxazole of the formula

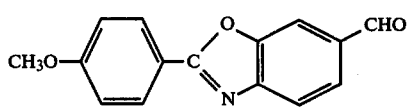

(melting point: 161.5°–162.5° C.) and 7.50 g (0.02 mole) of 2-(p-methoxyphenyl)-6-(diethylphosphonomethyl)-benzoxazole of the formula

(melting point: 85°–88° C.) in 150 ml of dimethyl formamide is heated to 50° C. and 2.1 g of sodium tert.butylate are added in small amounts to the solution over the course of 15 minutes. The reaction mixture is stirred at room temperature overnight, then poured into 400 ml of methanol with stirring. The product is collected by filtration, washed with water and then with 140 ml of methanol, and subsequently recrystallised from chlorobenzene with the addition of fuller's earth, affording 7.1 g (75% of theory) of 1,2-bis-(2-p-methoxyphenyl-benzoxazol-6-yl)-ethylene of the formula

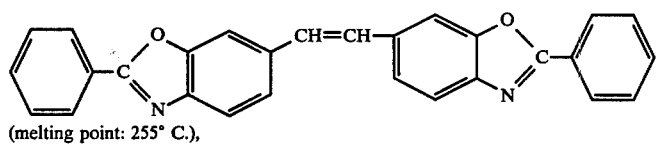

in the form of pale yellow crystals with a melting point of over 300° C.

Analysis: $C_{30}H_{22}N_2O_4$ (474.52); calculated: C 75.95 H 4.64 N 5.90; found: C 75.84 H 4.77 N 5.89.

By a procedure analogous to that described in this Example the following compounds of the formulae

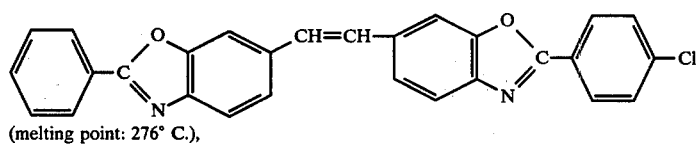

(melting point: 255° C.),

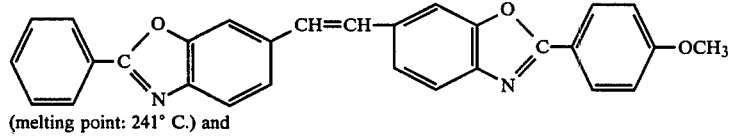

(melting point: 276° C.),

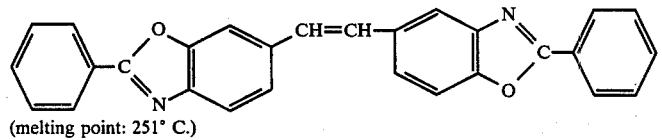

(melting point: 241° C.) and (melting point: 251° C.)

are obtained.

EXAMPLE 3

In a sulphonating flask which is provided with a water trap, 2.75 g (0.02 mole) of 4,5-dimethyl-2-aminophenol in 80 ml of xylene are stirred with 2.45 g (0.024 mole) of acetic anhydride for 1 hour at 60° C., and then 5.06 g (0.02 mole) of 2-(p-methoxyphenyl)-6-formyl-benzoxazole of the formula (112) and 4.35 g (0.013 mole) of toluene-4-sulphonic acid monohydrate are added to the xylene solution. The reaction mixture is stirred for 3 hours under reflux. The white suspension turns into a brown solution, in the process of which 1.9 ml of water are separated off by xylene/water azeotropic distillation. Then 70 ml of xylene are distilled off under normal pressure, the residue is cooled to 60° C. and 200 ml of methanol are added. The reaction mixture is cooled to room temperature and the precipitate is collected by filtration and washed with 60 ml of methanol, affording 5.1 g (64% of theory) of 1-[2-(6-methoxy-phenyl)-benzoxazol-6-yl]-2-(5,6-dimethylbenzoxazol-2-yl)-ethylene of the formula

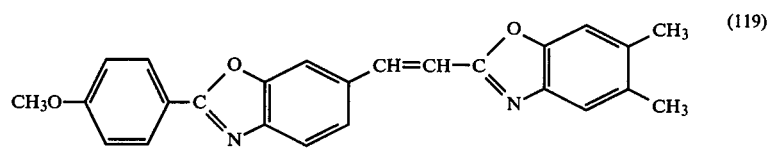

as a light yellow product. Recrystallisation from a solvent mixture of 350 ml of xylene and 350 ml of nonane with the addition of fuller's earth yields 4 g of greenish yellow crystals with a melting point of 223°-224° C.

Analysis: C$_{25}$H$_{20}$N$_2$O$_3$ (396.43); calculated: C 75.74 H 5.09 N 7.07; found: C 75.59 H 5.27 N 7.19.

The compounds of the formula

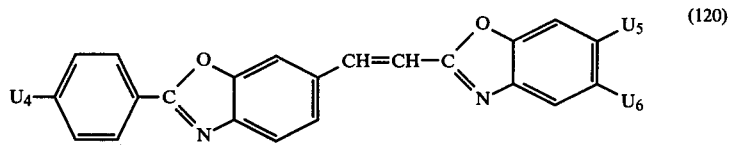

listed in Table II are obtained by the same process.

Table II

| No. | U$_4$ | U$_5$ | U$_6$ | melting point in °C. |
|---|---|---|---|---|
| 121 | OCH$_3$ | H | H | 209 |
| 122 | OCH$_3$ | H | CH$_2$CH$_2$CN | 226 |
| 123 | OCH$_3$ | H | –C$_6$H$_5$ | 221 |
| 124 | –C$_6$H$_5$ | H | H | 251 |
| 125 | –C$_6$H$_5$ | CH$_3$ | CH$_3$ | 238 |

EXAMPLE 4

A solution of 4.46 g (0.02 mole) of 2-phenyl-6-formyl-benzoxazole of the formula (101) and 6 g (0.021 mole) of methyl 4-diethylphosphonomethylbenzoate of the formula

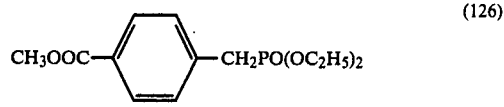

in 100 ml of dimethyl formamide is heated to 50° C. Then 2.1 g (0.022 mole) of sodium tert.butylate are added by small amounts to the solution in the course of 15 minutes and the resultant suspension is further stirred for 4 hours at room temperature. The reaction mixture is poured into water, and the precipitate is washed thoroughly with water and then with a total amount of 150 ml of methanol. The light brown product is recrystallised twice from nonane, affording 1.5 g (21% of theory) of 6-(carbomethoxystyryl)-2-phenyl-benzoxazole of the formula

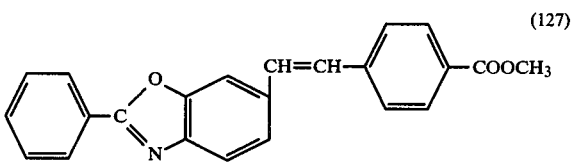

as pale yellow crystals with a melting point of 184°-185° C.

Analysis: C$_{23}$H$_{17}$NO$_3$ (355.40); calculated: C 77.73 H 4.82 N 3.94; found: C 77.70 H 5.00 N 4.00.

The benzoxazole-styryl compounds of the formula

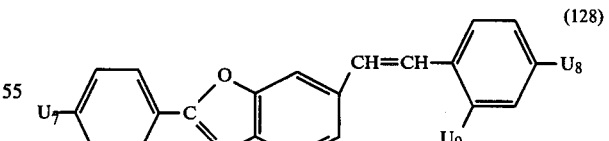

listed in Table III are obtained by repeating the procedure of this example.

Table III

| No. | U$_7$ | U$_8$ | U$_9$ | melting point in °C. |
|---|---|---|---|---|
| 129 | –C$_6$H$_5$ | H | CN | 199 |
| 130 | H | SO$_2$CH$_3$ | H | 236 |

Table III-continued

| No. | U7 | U8 | U9 | melting point in °C. |
|---|---|---|---|---|
| 131 | (phenyl) | SO3Na | SO3Na | * |
| 132 | (phenyl) | COOCH3 | H | 256 |
| 133 | Cl | COOCH3 | H | 211 |

* Compound 131 is purified as follows: 1 part of crude product is dissolved in 60 parts of dimethyl formamide. The solution is filtered using activated charcoal and the clear, warm solution of 60° C. is then diluted with 100 parts of ethyl acetate. After standing, the light beige-coloured product crystallises. It carbonises at temperatures above 340° C.

EXAMPLE 5

4.2 g (0.02 mole) of 2-(p-tolyl)-benzoxazole of the formula

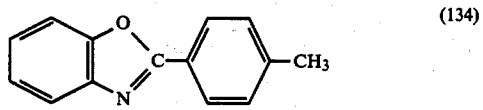

(134)

and 6.7 g (0.02 mole) of the Schiff's base, obtained from 2-phenyl-6-formyl-benzoxazole and o-chloroaniline, of the formula

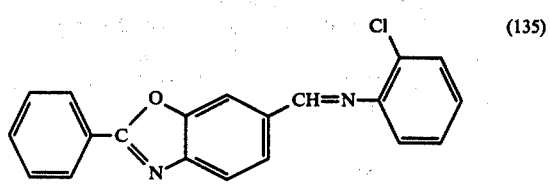

(135)

(melting point: 112.5°–113.5° C.) are dissolved in 80 ml of dimethyl formamide. To this solution are added in small amounts in the course of 20 minutes 2.1 g (0.002 mole) of sodium tert.butylate at 20° to 25° C. while introducing nitrogen. During the first 10 minutes, the reaction mixture is irradiated with ultraviolet light. While further introducing nitrogen and stirring for 2 hours at 20° to 25° C. the colour of the mixture changes gradually from yellow through violet brown to brown. Then 320 ml of methanol are added and the batch is cooled to 0° C. The precipitate is collected by filtration, washed repeatedly with a total of 40 ml of methanol and dried, affording 3.2 g (39% of theory) of 1-(2-phenyl-benzoxazol-6-yl)-2-(4'-benzoxazol-2-yl-phenyl)-ethylene of the formula

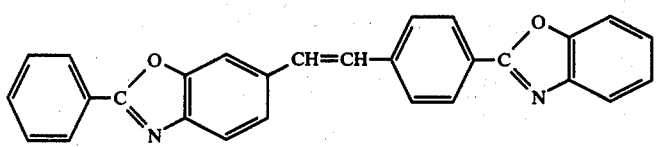

in the form of a light beige-coloured powder with a melting point of 233°–237° C.

Recrystallisation from toluene with the addition of fuller's earth yields 2.9 g (35.4% of theory) of pale yellow crystals which melt at 236°–237° C.

Analysis: $C_{28}H_{18}N_2O_2$ (414.44); calculated: C 81.14 H 4.38 N 6.76; found: C 81.04 H 4.50 N 6.90.

The starting materials required in Examples 1 to 5 can be obtained as follows:

A. Manufacture of the methyl- and formyl-benzoxazole compounds (a) A sulphonating flask is charged with 123 g (1 mole) of 6-amino-m-cresol in 1500 ml of dioxan, then 92.4 g (1.1 mole) of sodium bicarbonate are added and a solution of 170.6 g (1 mole) of p-methoxybenzoyl chloride in 200 ml of dioxan is added dropwise in the course of 15 minutes. The suspension is heated to 55° C. for 3 hours, then the reaction mixture is poured into 6 liters of water, acidified with conc. hydrochlorid acid to pH 2 to 3, and the precipitate is collected by filtration. The filter cake is thoroughly washed neutral with water, affording 197.7 g (76.8% of theory) of the compound of the formula

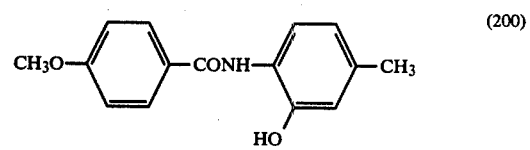

(200)

in the form of a light brown product with a melting point of 168°–169° C.

The compounds listed in Table IV can be prepared in analogous manner.

Table IV (207)

| No. | X1 | X2 | X3 | X4 | melting point in °C. |
|---|---|---|---|---|---|
| 202 | H | H | CH3 | H | 167–168 |
| 203 | ClCH2 | H | H | H | 172–173 |
| 204 | H | H | H | CH3 | 192–194 |
| 205 | Cl | H | CH3 | H | 215–217 |
| 206 | (phenyl) | H | CH3 | H | 216–218 |
| 207 | ClCH2 | CH3 | H | CH3 | 165–167 |
| 208 | ClCH2 | H | H | (CH3)3C | 171–175 |
| 209 | ClCH2 | H | H | Cl | 226–227 |

(b) In a sulphonating flask which is equipped with a water trap, 197.7 g (0.77 mole) of the compound of the formula (200) and 4.35 g (0.023 mole) of toluene-4-sulphonic acid monohydrate in 1500 ml of o-dichlorobenzene are stirred for 5 hours under reflux, while 15 ml of water are removed by azeotropic distillation. The reaction mixture is concentrated, in the process of which 1200 ml of dichlorobenzene are distilled off. The residue is dissolved hot in 1000 ml of xylene, and the solution is filtered hot using fuller's earth, concentrated to 300 ml and poured into 2000 ml of hexane. The precipitate is collected by filtration at 10° C., affording 193 g (81% of theory) of the compound of the formula $$CH_3O-\phi-C(=N)-O-\text{benzoxazole}-CH_3 \quad (210)$$

in the form of a light beige-coloured product with a melting point of 89° to 92° C. Recrystallisation from hexane with the aid of fuller's earth yields white crystals with a melting point of 91.5°–92° C.

The compounds listed in Table V can be obtained in analogous manner.

Table V $$X_1'-\phi-C(=N)-O-\text{benzoxazole}(X_2', X_3', X_4') \quad (211)$$

| No. | $X_1'$ | $X_2'$ | $X_3'$ | $X_4'$ | melting point in °C. |
|-----|--------|--------|--------|--------|---------------------|
| 212 | H | H | CH$_3$ | H | 90–92 |
| 213 | H$_3$C | H | H | H | 115–116 |
| 214 | ClCH$_2$ | H | H | H | 143–146 |
| 215 | H | H | H | CH$_3$ | 105–107 |
| 216 | Cl | H | CH$_3$ | H | 152–153 |
| 217 | phenyl | H | CH$_3$ | H | 160–161 |
| 218 | ClCH$_2$ | CH$_3$ | H | CH$_3$ | 118–119 |
| 219 | ClCH$_2$ | H | H | (CH$_3$)$_3$C | 143–144 |
| 220 | ClCH$_2$ | H | H | Cl | 167–169 |

(c) In sulphonating flask, 140 g (0.585 mole) of 2-(p-methoxyphenyl)-6-methyl-benzoxazole (compound of the formula (210)) and 109.3 g (0.614 mole) of N-bromosuccinimide are dissolved in 1400 ml of carbon tetrachloride. Then 100 mg of dibenzoyl peroxide are added and the reaction mixture is stirred for 4 hours at reflux temperature and under irradiation with a 500 watt halogen lamp. The suspension is filtered by suction and the residue is suspended in warm water. The aqueous suspension is filtered once more and the water-insoluble residue is added to the carbon tetrachloride filtrate. The red carbon tetrachloride filtrate is concentrated to dryness, affording 178 g of light brown product (95.6% of theory) with a melting point of 119°–127° C.

The crude product is recrystallised from a solvent mixture of dimethyl formamide/isopropanol (1:4), ultimately yielding 139 g (74.6% of theory) of 2-(p-methoxyphenyl)-6-bromomethyl-benzoxazole of the formula $$CH_3O-\phi-C(=N)-O-\text{benzoxazole}-CH_2Br \quad (221)$$

in the form of a light beige-coloured product with a melting point of 137°–138° C.

The compounds of the formula $$X_1''-\phi-C(=N)-O-\text{benzoxazole}(X_3'', X_4'') \quad (222)$$

listed in Table VI can be prepared in analogous manner.

Table VI

| No. | $X_1''$ | $X_3''$ | $X_4''$x | melting point in °C. |
|-----|---------|---------|----------|---------------------|
| 223 | H | CH$_2$Br | H | 133–135 |
| 224 | H | H | CH$_2$Br | 172–173 |
| 225 | Cl | CH$_2$Br | H | 163–164 |
| 226 | phenyl | CH$_2$Br | H | 137–138 |

(d) A sulphonating flask is charged with 1200 ml of anhydrous ethanol and 7.31 g (0.318 mole) of sodium are dissolved therein under a flow of nitrogen and then 36.75 g (0.413 mole) of 2-nitropropane are added at 30° C. The solution is stirred for 1 hour at room temperature. A solution of 101 g (0.318 mole) of 2-(p-methoxyphenyl)-6-bromomethyl-benzoxazole (compound of the formula (221)) in 300 ml of dimethyl formamide is then added to the reaction mixture and the brown solution is stirred for 20 hours at room temperature. The suspension is filtered at −5° C. and the filter cake is suspended in methanol. This suspension is filtered and the filter cake is dried at room temperature in vacuo, affording 64.7 g (80.5% of theory) of a light beige-coloured product of the formula $$CH_3O-\phi-C(=N)-O-\text{benzoxazole}-CHO \quad (112)$$

with a melting point of 161.5°–162.5° C.

The compound of the formula (112) can also be obtained from the corresponding chloromethyl compound by the above procedure.

The compounds of the formula $$X_1'''-\phi-C(=N)-O-\text{benzoxazole}(X_3''', X_4''') \quad (227)$$

listed in Table VII can be prepared in analogous manner.

Table VII

| No. | $X_1'''$ | $X_3'''$ | $X_4'''$ | melting point in °C. |
|-----|----------|----------|----------|---------------------|
| 101 | H | CHO | H | 134–135 |
| 228 | CHO | H | H | 173–174 |
| 229 | H | H | CHO | 163–164 |
| 230 | Cl | CHO | H | 146–148 |
| 231 | phenyl | CHO | H | 201–203 |

B. Manufacture of the phosphonomethyl-benzoxazole compounds

A round bottom flask is charged with 38 g (0.12 mole) of 2-(p-methoxyphenyl)-6-bromomethyl-benzoxazole (compound of the formula (221)) in 38 ml of triethylphosphite and the reaction mixture is heated to 150° C., kept for 30 minutes at this temperature and then excess triethylphosphite is distilled off in vacuo (10 mm). The residue, a brown oil, congeals after 10 hours. The crude product (44.5 g =98.9% of theory) is stirred with hexane in a mixer. The fine crystalline suspension is filtered by suction and the filter cake is washed with hexane, affording 40 g (88.9% of theory) of 6-(diethylphosphonomethyl)-2-(p-methoxyphenyl)-benzoxazole of the formula

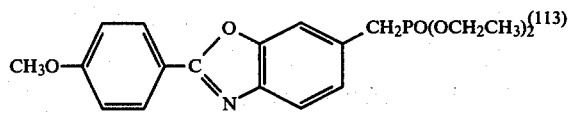

in the form of light beige-coloured crystals with a melting point of 86°–88° C.

The compound (113) can also be prepared from the corresponding chloromethyl compound using triethylphosphite at 150° C.

The compounds of the formula

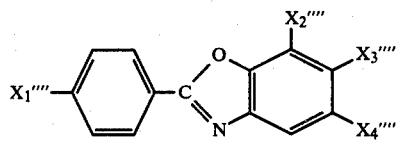

listed in Table VIII can be obtained in analogous manner from the bromomethyl compounds of the formulae (221) to (226) or from the chloromethyl compounds of the formulae (214) and (218) to (220).

Table VIII

| No. | $X_1''''$ | $X_2''''$ | $X_3''''$ | $X_4''''$ | melting point in °C. |
|---|---|---|---|---|---|
| 233 | H | H | $CH_2PO(OC_2H_5)_2$ | H | yellow oil |
| 234 | $CH_2PO(OC_2H_5)_2$ | H | H | H | 72–75 |
| 235 | H | H | H | $CH_2PO(OC_2H_5)_2$ | 134–135 |
| 236 | $CH_2PO(OC_2H_5)_2$ | $CH_3$ | H | $CH_3$ | 78–79 |
| 237 | $CH_2PO(OC_2H_5)_2$ | H | H | $C(CH_3)_3$ | 89–90 |
| 238 | $CH_2PO(OC_2H_5)_2$ | H | H | Cl | 96–98 |
| 239 | Cl | H | $CH_2PO(OC_2H_5)_2$ | H | 117–120 |
| 240 | 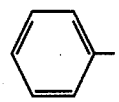 | H | $CH_2PO(OC_2H_5)_2$ | H | 78–80 |

The starting material for the manufacture of the compound of the formula (129) (Example 4), viz. 2-diethylphosphonomethylbenzonitrile (b.p. 150°–152° C. at 0.3 mm) of the formula

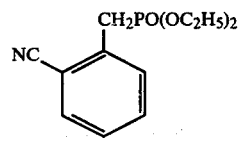

is prepared from 2-chloromethyl-benzonitrile (melting point 55°–58° C.) by treatment with triethylphosphite at 150° C. and subsequent fractional distillation in vacuo.

In similar manner, the compound of the formula (126), viz. methyl 4-diethylphosphonomethylbenzoate of the formula

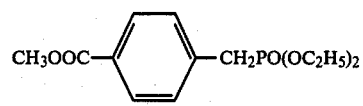

is obtained from methyl 4-chloromethylbenzoate (b.p. 137° C. at 9 mm) as a light yellow oil by treatment with triethylphosphite at 150° C. and subsequent distillation of excess triethylphosphite.

C. Preparation of the starting material for the manufacture of the compound of the formula (122) (Example 3)

namely 3-(m-amino-p-hydroxyphenyl)-propionitrile of the formula

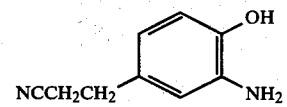

3-(p-hydroxyphenyl)-propionitrile is nitrated in glacial acetic acid with 65% nitric acid at 10° to 15° C. in the course of 2 hours and the resultant 3-(m-nitro-p-hydroxyphenyl)-propionitrile (m.p. 104° C.) is reduced in ethanol at room temperature with hydrogen, using 5% palladium on charcoal as catalyst, to 3-(m-amino-p-hydroxyphenyl)-propionitrile with a melting point of 125° C.

D. Preparation of the Schiff's base of the formula (135)

22.3 g (0.1 mole) of 2-phenyl-6-formyl-benzoxazole (compound (101)), 12.7 g (0.1 mole) of o-chloroaniline and 0.2 g of boric acid are stirred in 50 ml of xylene for ½ hour under reflux, while the water formed during the reaction is removed by means of a water trap. After cooling to 70° C., 300 ml of methanol are added. The resulting suspension is cooled to −10° C. and the crystallised product is collected by filtration and dried in vacuo, affording 26.6 g (80% of theory) of the compound of the formula (135) in the form of almost white crystals with a melting point of 112°–113° C.

EXAMPLE 6

Polyester fabric (25 g) is put into a bath (liquor ratio 1:40) which contains, per liter, 10 g of a condensation product of aromatic sulphonic acids, 25 g of an aromatic carboxylic acid ester as emulsifier and 5 g of sodium dihydrophosphate. The pH is adjusted to 5 with acetic acid. After a treatment time of one hour at boiling temperature in the presence of 0.05 g/l of a fluorescent brightening agent of the formula (129), the fabric has a brilliant white effect of good light fastness.

EXAMPLE 7

100 Parts of granulated terephthalic acid/ethylene glycol-polyester are homogeneously mixed with 0.05 part of one of the compounds of the formulae (105), (115), (130), (132) or (129) and the mixture is fused at 285° C. and spun through conventional spinnerets. Strongly whitened polyester fibres of good lightfastness are obtained. The above compounds can also be added to the starting materials before or during the polycondensation to the polyester.

EXAMPLE 8

A polyester fabric (e.g. "Dacron") is padded at room temperature (about 20° C.) with an aqueous dispersion which contains, per liter, 2 g of one of the compounds of the formulae (105), (115), (132), (133) or (129) as well as 1 g of an adduct of about 8 moles of ethylene oxide and 1 mole of p-tert-octylphenol, and dried at about 100° C. The dry material is subsequently subjected to a heat treatment of 170° to 220° C., which lasts from 2 minutes to a few seconds, depending on the temperature. The treated material shows a strong white effect of good lightfastness.

EXAMPLE 9

To 100 ml of water is added 0.06 g of Tinegal NA ® (alkylpolyglycol ether). A solution of a fluorescent brightening agent of the formula (130) is prepared by dissolving 1 g in 1000 ml of dimethyl formamide. Then 3 ml of this stock solution are added to the above solution. This aqueous solution or dispersion which contains the fluorescent brightening agent is heated to 60° C. and then a nylon fabric weighing 3 g is put thereinto. The temperature is raised in the course of 10 to 15 minutes to 92°–95° C. and kept thereat for 30 minutes. The fabric is then rinsed for 2 minutes in running cold water and subsequently dried at 60° C. The treated fabric has a marked white effect of good lightfastness.

Analogous effects are obtained with the fluorescent brightening agents of the formulae (115) or (129).

EXAMPLE 10

A polyamide fabric (Perlon) is put at 60° C., in a liquor ratio of 1:40, into a bath which contains (based on the weight of the fabric) 0.1% of one of the fluorescent brightening agents of the formulae (130), (115) or (129) and, per liter, 1 g of 80% acetic acid and 0.25 g of an adduct of 30 to 35 moles of ethylene oxide and 1 mole of technical quality stearyl alcohol. The bath is heated in the course of 30 minutes to boiling temperature and kept at the boil for 30 minutes. The fabric is then rinsed and dried. A strong white effect of good light fastness is obtained.

Similar white effects are obtained by using a fabric made of polyamide 66 (nylon) instead of polyamide 6.

Finally, it is also possible to carry out the process under high temperature conditions, e.g. over the course of 30 minutes at 130° C. For this kind of application it is advisable to add 3 g/l of hydrosulphite to the liquor.

EXAMPLE 11

Nylon fabric is washed in a liquor ratio of 1:20 for 15 minutes in a warm liquor of 55° C. which contains, per liter, 0.008 g of a fluorescent brightening agent of the formula (130) and 4 g of a detergent of the following composition:

| | |
|---|---|
| alkylarylsulphonate | 15.7% |
| fatty alcohol sulphate | 3.7% |
| coconut acid monoethanolamide | 39.0% |
| sodium silicate | 4.0% |
| magnesium silicate | 2.0% |
| carboxymethyl cellulose | 1.0% |
| sodium ethylenediaminetetraacetate | 0.5% |
| water | 6.7% |
| sodium sulphate to make up | 100% |

Thereafter the fabric is washed for ½ minute under running water and dried at 60° C. for 20 minutes in a drying cabinet. The fabric has a strong white effect of good lightfastness. The fluorescent brightener of the formula (130) can also be incorporated direct into the detergent of the above composition. Similar effects are also obtained using the fluorescent brightening agents of the formulae (115), (131) and (129).

What is claimed is:

1. Benzoxazole compounds of the formula

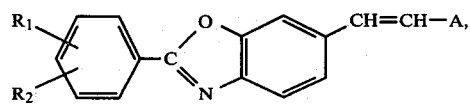

wherein

R$_1$ represents hydrogen, halogen, cyano, alkyl of 1 to 8 carbon atoms, cyclohexyl, alkyl of 1 to 4 carbon atoms which is substituted by halogen, cyano, alkoxy of 1 to 4 carbon atoms or phenyl, while the phenyl moiety of a phenylalkyl radical can contain in addition one or two substituents selected from the group consisting of halogen, methyl or methoxy; alkoxy of 1 to 4 carbon atoms which is unsubstituted or substituted by cyano or alkoxy of 1 to 4 carbon atoms; phenyl or phenoxy which is unsubstituted or substituted by one or two radicals selected from the group consisting of halogen, cyano, alkyl or alkoxy, each of 1 to 4 carbon atoms; the sulpho group and the derivatives thereof; the carboxyl group and the derivatives thereof; a sulphonyl group; or together with R$_2$ in the ortho-position represents an alkylene radical of 3 or 4 carbon atoms or the butadienylene radical, R$_2$ represents hydrogen, alkyl of 1 to 6 carbon atoms, alkoxy of 1 to 4 carbon atoms, halogen, or together with R$_1$ in the ortho-position represents an alkylene radical of 3 or 4 carbon atoms or the butadienylene radical, and A represents a group of the formula

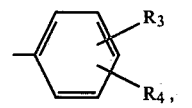

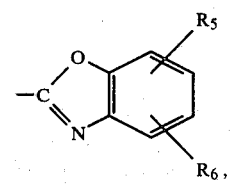

-continued or

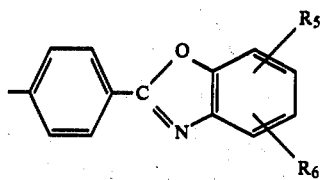

wherein
R₃ represents a carboxyl group and the derivatives thereof, a sulpho group and the salts thereof, a sulphonyl or cyano group, R₄ represents hydrogen, alkyl of 1 to 6 carbon atoms, alkoxy of 1 to 4 carbon atoms, halogen, the sulpho group and the salts thereof or the carboxyl group and the derivatives thereof, R₅ represents hydrogen, alkyl of 1 to 8 carbon atoms, alkyl of 1 to 4 carbon atoms which is substituted by halogen, cyano, alkoxy of 1 to 4 carbon atoms or phenyl, while the phenyl moiety of a phenylalkyl radical can contain in addition one or two substituents selected from the group consisting of halogen, methyl or methoxy; cyclohexyl; alkoxy of 1 to 4 carbon atoms which is unsubstituted or substituted by cyano or alkoxy of 1 to 4 carbon atoms; phenyl or phenoxy which is unsubstituted or substituted by one or two radicals selected from the group consisting of halogen, cyano, alkyl or alkoxy, each of 1 to 4 carbon atoms; halogen, cyano, sulphonyl, the carboxyl group or the derivatives thereof; the sulpho group or the derivatives thereof; or together with R₆ in the ortho-position represents an alkylene radical of 3 or 4 carbon atoms or the butadienylene radical; and R₆ represents hydrogen, alkyl of 1 to 6 carbon atoms, alkoxy of 1 to 4 carbon atoms, halogen, or together with R₅ in the ortho-position represents an alkylene radical of 3 or 4 carbon atoms or the butadienylene radical.

2. Benzoxazole compounds according to claim 1 of the formula

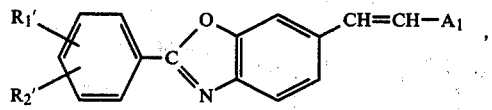

wherein
R₁' represents hydrogen, alkyl of 1 to 4 carbon atoms, cyanoalkyl containing 1 to 3 carbon atoms in the alkyl moiety, alkoxyalkyl having a total of 2 to 6 carbon atoms, halogen, cyano, benzyl, alkoxy of 1 to 4 carbon atoms, alkoxyalkoxy having a total of 2 to 6 carbon atoms, phenyl, phenoxy, carbalkoxy of 2 to 5 carbon atoms, the carboxyl group and the alkali metal, alkaline earth metal, ammonium and amine salts thereof, or together with R₂' in the ortho-position represents the butadienylene radical, R₂' represents hydrogen, alkyl of 1 to 4 carbon atoms, halogen, alkoxy of 1 to 4 carbon atoms, or together with R₁' in the ortho-position represents the butadienylene radical; and A₁ represents a group of the formula

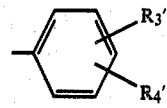

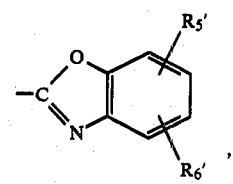

or

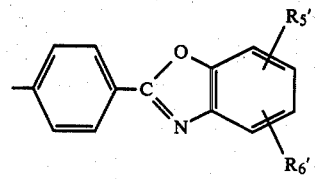

wherein
R₃' represents alkylsulphonyl of 1 to 4 carbon atoms, cyano, a group of the formula —COOY, in which Y represents hydrogen, alkyl of 1 to 4 carbon atoms or an alkali metal, alkaline earth metal, ammonium or amine ion; or represents a group of the formula —SO₃Y₁, in which Y₁ represents hydrogen, an alkali metal, alkaline earth metal, ammonium or amine ion, R₄' represents hydrogen, alkyl of 1 to 4 carbon atoms, alkoxy of 1 to 4 carbon atoms, halogen, or the sulpho group and the alkali metal salts thereof, R₅' represents hydrogen, alkyl of 1 to 4 carbon atoms, alkoxyalkyl having a total of 2 to 6 carbon atoms, cyanoalkyl containing 1 to 3 carbon atoms in the alkyl moiety, benzyl, alkoxy of 1 to 4 carbon atoms, alkoxyalkoxy of 2 to 6 carbon atoms, phenyl, phenoxy, halogen, cyano, alkylsulphonyl of 1 to 4 carbon atoms, a group of the formula —COOY, in which Y represents hydrogen, alkyl of 1 to 4 carbon atoms or an alkali metal, alkaline earth metal, ammonium or amine ion; or represents a group of the formula —SO₃Y₁, in which Y₁ represents hydrogen, an alkali metal, alkaline earth metal, ammonium or amine ion, a group of the formula

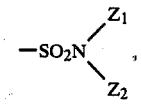

in which Z₁ represents hydrogen, alkyl of 1 to 4 carbon atoms, alkoxyalkyl having a total of 2 to 6 carbon atoms, cyanoalkyl containing 1 to 3 carbon atoms in the alkyl moiety, Z₂ has the meaning of Z₁ and in addition represents benzyl, or Z₁ or Z₂ together with the nitrogen atom to which they are attached form a morpholine or piperidine ring, or together with R₆' in the ortho-position represent the butadienylene radical; and R₆' represents hydrogen, alkyl of 1 to 4 carbon atoms, alkoxy of 1 to 4 carbon atoms or halogen, or together with R₅' in the ortho-position represents the butadienylene radical, 3. Benzoxazole compounds according to claim 2 of the formula

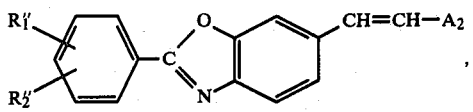

wherein
- $R_1''$ represents hydrogen, alkyl of 1 to 4 carbon atoms, halogen, cyano, alkoxy of 1 to 4 carbon atoms, phenyl, the carboxyl group and the alkali metal salts thereof, carbalkoxy of 2 to 5 carbon atoms, or together with $R_2''$ in the ortho-position represents the butadienylene radical,
- $R_2''$ represents hydrogen, alkyl of 1 to 4 carbon atoms, halogen, alkoxy of 1 to 4 carbon atoms, or together with $R_1''$ in the ortho-position represents the butadienylene radical, and
- $A_2$ represents a group of the formula

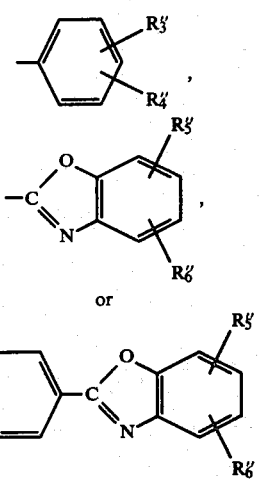

wherein
- $R_3''$ represents alkylsulphonyl of 1 to 4 carbon atoms, cyano, the carboxyl group and the alkali metal salts thereof, carbalkoxy of 2 to 5 carbon atoms, the sulpho group and the alkali metal salts thereof,
- $R_4''$ represents hydrogen, alkyl of 1 to 4 carbon atoms, alkoxy of 1 to 4 carbon atoms, halogen or the sulpho group and the alkali metal salts thereof,
- $R_5''$ represents hydrogen, alkyl of 1 to 4 carbon atoms, alkoxyalkyl having a total of 2 to 6 carbon atoms, cyanoalkyl containing 1 to 3 carbon atoms in the alkyl moiety, alkoxy of 1 to 4 carbon atoms, phenyl, halogen, cyano, alkylsulphonyl of 1 to 4 carbon atoms, the carboxyl group and the alkali metal salts thereof, carbalkoxy of 2 to 5 carbon atoms, the sulpho group and the alkali metal salts thereof; and
- $R_6''$ represents hydrogen, alkyl of 1 to 4 carbon atoms, alkoxy of 1 to 4 carbon atoms or halogen.

4. Benzoxazole compounds according to claim 2 of the formula

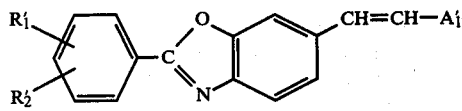

wherein $R_1'$ and $R_2'$ are as defined in claim 2 and $A_1'$ represents a group of the formula

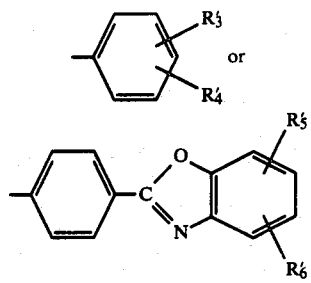

or

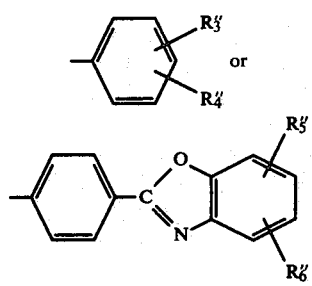

wherein $R_3'$, $R_4'$, $R_5'$ and $R_6'$ are as defined in claim 2.

5. Benzoxazole compounds according to claim 3 of the formula

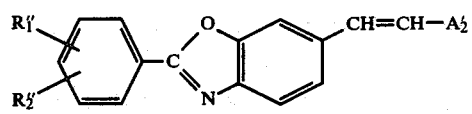

wherein $R_1''$ and $R_2''$ are as defined in claim 3 and $A_2'$ represents a group of the formula

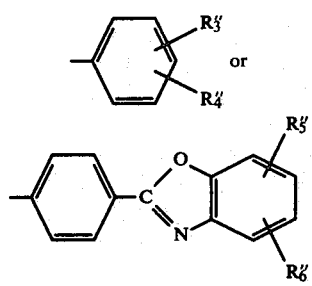

wherein $R_3''$, $R_4''$, $R_5''$ and $R_6''$ are as defined in claim 3.

6. Benzoxazole compounds according to claim 5 of the formula

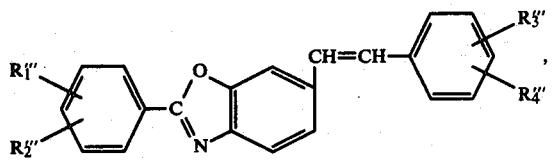

wherein
- $R_1'''$ represents hydrogen, alkyl of 1 to 4 carbon atoms, halogen, cyano, alkoxy of 1 to 4 carbon atoms, or phenyl,
- $R_2'''$ represents hydrogen, alkyl of 1 to 4 carbon atoms, halogen, or alkoxy of 1 to 4 carbon atoms,
- $R_3'''$ represents alkylsulphonyl of 1 to 4 carbon atoms, cyano, the carboxyl group and the alkali metal salts thereof, carbalkoxy of 2 to 5 carbon atoms, or the sulpho group and the alkali metal salts thereof; and
- $R_4'''$ represents hydrogen, alkyl of 1 to 4 carbon atoms, alkoxy of 1 to 4 carbon atoms, halogen or the sulpho group and the alkali metal salts thereof.

7. Benzoxazole compounds according to claim 6 of the formula

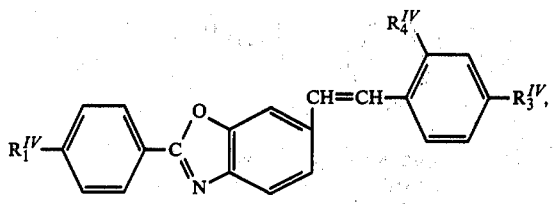

wherein
$R_1^{IV}$ represents hydrogen, chlorine, phenyl, or alkoxy of 1 to 4 carbon atoms,
$R_3^{IV}$ represents alkylsulphonyl of 1 to 4 carbon atoms, carbalkoxy of 2 to 5 carbon atoms, cyano, or the sulpho group and the alkali metal salts thereof, and
$R_4^{IV}$ represents hydrogen or the sulpho group and the alkali metal salts thereof.

8. A benzoxazole compound according to claim 6 of the formula

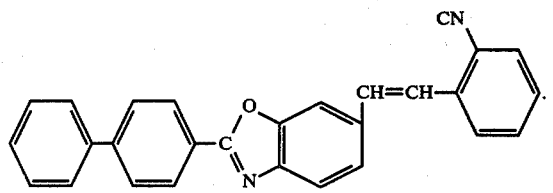

9. Benzoxazole compounds according to claim 5 of the formula

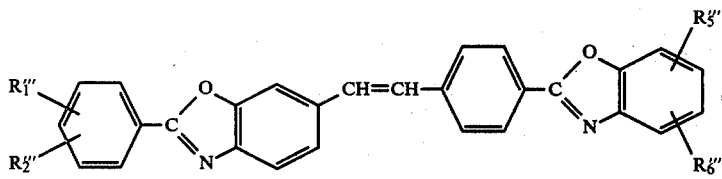

wherein
$R_1'''$ represents hydrogen, alkyl of 1 to 4 carbon atoms, halogen, cyano, alkoxy of 1 to 4 carbon atoms or phenyl,
$R_2'''$ represents hydrogen, alkyl of 1 to 4 carbon atoms, halogen, or alkoxy of 1 to 4 carbon atoms,
$R_5'''$ represents hydrogen, alkyl of 1 to 4 carbon atoms, cyanoalkyl containing 1 to 3 carbon atoms in the alkyl moiety, alkoxy of 1 to 4 carbon atoms, phenyl, chlorine or cyano; and
$R_6'''$ represents hydrogen, alkyl of 1 to 4 carbon atoms, alkoxy of 1 to 4 carbon atoms or chlorine.

10. Benzoxazole compounds according to claim 9 of the formula

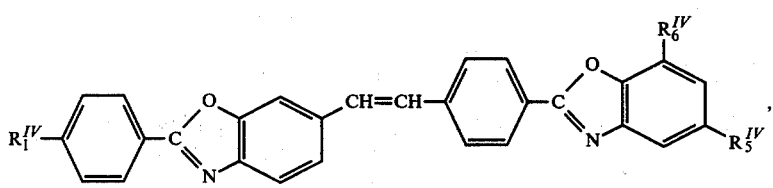

wherein
$R_1^{IV}$ represents hydrogen, chlorine, alkoxy of 1 to 4 carbon atoms, or phenyl,
$R_5^{IV}$ represents hydrogen, chlorine or alkyl of 1 to 4 carbon atoms, and $R_6^{IV}$ represents hydrogen or alkyl of 1 to 4 carbon atoms.

11. Benzoxazole compounds according to claim 3 of the formula

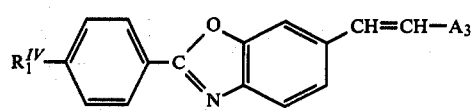

wherein
$R_1^{IV}$ represents hydrogen, chlorine, alkoxy of 1 to 4 carbon atoms or phenyl, and
$A_3$ represents a group of the formula

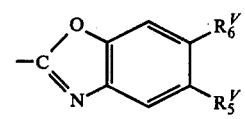

wherein
$R_5^V$ represents hydrogen, alkyl of 1 to 4 carbon atoms, cyanoalkyl having a total of 2 or 3 carbon atoms, or phenyl, and
$R_6^V$ represents hydrogen or alkyl of 1 to 4 carbon atoms.

12. A process for the manufacture of benzoxazole compounds of the formula

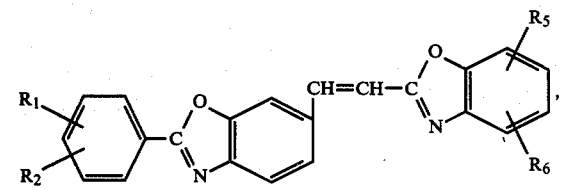

wherein
$R_1$ represents hydrogen, halogen, cyano, alkyl of 1 to 8 carbon atoms, cyclohexyl, alkyl of 1 to 4 carbon atoms which is substituted by halogen, cyano, alkoxy of 1 to 4 carbon atoms or phenyl, while the phenyl moiety of a phenylalkyl radical can contain in addition one or two substituents selected from the group consisting of halogen, methyl or methoxy; alkoxy of 1 to 4 carbon atoms which is unsubstituted or substituted by cyano or alkoxy of 1 to 4 carbon atoms; phenyl or phenoxy which is unsubstituted or substituted by one or two radicals selected from the group consisting of halogen, cyano, alkyl or alkoxy, each of 1 to 4 carbon atoms; the sulpho group and the derivatives thereof; the carboxyl group and the derivatives thereof; a sulphonyl group; or together with R₂ in the ortho-position represents an alkylene radical of 3 or 4 carbon atoms or the butadienylene radical, R₂ represents hydrogen, alkyl of 1 to 6 carbon atoms, alkoxy of 1 to 4 carbon atoms, halogen, or together with R₁ in the ortho-position represents an alkylene radical of 3 or 4 carbon atoms or the butadienylene radical, R₅ represents hydrogen, alkyl of 1 to 8 carbon atoms, alkyl of 1 to 4 carbon atoms which is substituted by halogen, cyano, alkoxy of 1 to 4 carbon atoms or phenyl, while the phenyl moiety of a phenylalkyl radical can contain in addition one or two substituents selected from the group consisting of halogen, methyl or methoxy; cyclohexyl, alkoxy of 1 to 4 carbon atoms which is unsubstituted or substituted by cyano or alkoxy of 1 to 4 carbon atoms; phenyl or phenoxy which is unsubstituted or substituted by one or two radicals selected from the group consisting of halogen, cyano, alkyl or alkoxy, each of 1 to 4 carbon atoms; halogen, cyano, sulphony, the carboxyl group or the derivatives thereof, the sulpho group or the derivatives thereof; or together with R₆ in the ortho-position represents an alkylene radical of 3 or 4 carbon atoms or the butadienylene radical; and R₆ represents hydrogen, alkyl of 1 to 6 carbon atoms, alkoxy of 1 to 4 carbon atoms, halogen, or together with R₅ in the ortho-position represents an alkylene radical of 3 or 4 carbon atoms or the butadienylene radical, which process comprises reacting an o-aminophenol of the formula

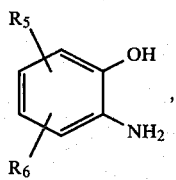

wherein R₅ and R₆ have the given meanings, in an inert high-boiling solvent, with acetic anhydride and an aldehyde of the formula

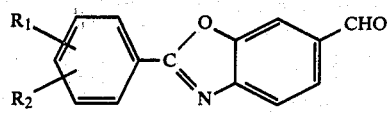

wherein R₁ and R₂ have the given meanings, using a catalyst which splits off water, and without isolation of an intermediate.

13. A process according to claim 12 for the manufacture of benzoxazole compounds of the formula

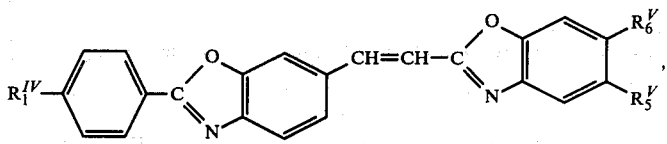

wherein $R_1'^v$ represents hydrogen, chlorine, alkoxy of 1 to 4 carbon atoms or phenyl, $R_5^v$ represents hydrogen, alkyl of 1 to 4 carbon atoms, cyanoalkyl having a total of 2 or 3 carbon atoms or phenyl, and $R_6^v$ represents hydrogen or alkyl of 1 to 4 carbon atoms, which process comprises reacting an o-aminophenol of the formula

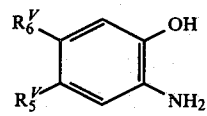

in which $R_5^v$ and $R_6^v$ have the given meanings, with acetic anhydride and an aldehyde of the formula

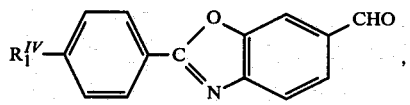

in which $R_1'^v$ has the given meaning.

14. A process according to claim 12 which is carried out in a high-boiling aromatic hydrocarbon using toluene-4-sulphonic acid as catalyst and the water of reaction is continuously removed.

15. A method of optically brightening organic material which comprises incorporating in said material or applying to the surface thereof a compound as defined in claim 1.

16. A method according to claim 15 wherein synthetic organic material of high molecular weight, preferably of polyester and polyamide, is brightened.

17. A method according to claim 16 wherein the fluorescent brightening agent is incorporated into spinning solutions/melts of polyester or polyamide and these latter are subsequently spun.

18. A method according to claim 16 wherein polyester or polyamide fabrics are brightened by the pad-heat process.

19. A method according to claim 15 wherein 0.001 to 2%, preferably 0.01 to 0.5%, of the fluorescent brightening agent, based on the weight of the material to be brightened, is applied to said material or incorporated thereinto.

* * * * *

UNITED STATES PATENT AND TRADEMARK OFFICE
CERTIFICATE OF CORRECTION

PATENT NO. : 4,167,628
DATED : September 11, 1979
INVENTOR(S) : Geza Kormany

It is certified that error appears in the above-identified patent and that said Letters Patent are hereby corrected as shown below:

In Assignee [73]: "Ciba-Geigy Corporation, Ardsley, N.J."

should be -- Ciba-Geigy Corporation, Ardsley, N.Y.--.

Signed and Sealed this

Eighth Day of April 1980

[SEAL]

Attest:

SIDNEY A. DIAMOND

Attesting Officer

Commissioner of Patents and Trademarks